(12) United States Patent
Li et al.

(10) Patent No.: US 9,629,884 B2
(45) Date of Patent: Apr. 25, 2017

(54) COMPOSITIONS AND METHODS FOR INCREASING LIFESPAN AND HEALTH SPAN

(75) Inventors: Ming Li, New Territories (HK); Lei Cheng, Quarry Bay (HK)

(73) Assignee: GENEREX PHARMACEUTICALS, INC., George Town (KY)

( * ) Notice: Subject to any disclaimer, the term of this patent is extended or adjusted under 35 U.S.C. 154(b) by 0 days.

(21) Appl. No.: 13/377,501

(22) PCT Filed: Jun. 11, 2010
(Under 37 CFR 1.47)

(86) PCT No.: PCT/IB2010/001426
§ 371 (c)(1),
(2), (4) Date: Feb. 20, 2012

(87) PCT Pub. No.: WO2010/143065
PCT Pub. Date: Dec. 16, 2010

(65) Prior Publication Data
US 2012/0177759 A1    Jul. 12, 2012

Related U.S. Application Data

(60) Provisional application No. 61/186,709, filed on Jun. 12, 2009, provisional application No. 61/187,905, filed on Jun. 17, 2009.

(51) Int. Cl.
| | | |
|---|---|---|
| *A61K 36/00* | (2006.01) | |
| *A61K 31/56* | (2006.01) | |
| *A61K 31/565* | (2006.01) | |
| *A61K 31/7028* | (2006.01) | |
| *A61K 31/7032* | (2006.01) | |
| *A61K 31/7034* | (2006.01) | |
| *A61K 36/23* | (2006.01) | |
| *A61K 36/73* | (2006.01) | |

(52) U.S. Cl.
CPC .............. *A61K 36/00* (2013.01); *A61K 31/56* (2013.01); *A61K 31/565* (2013.01); *A61K 31/7028* (2013.01); *A61K 31/7032* (2013.01); *A61K 31/7034* (2013.01); *A61K 36/23* (2013.01); *A61K 36/73* (2013.01)

(58) Field of Classification Search
None
See application file for complete search history.

(56) References Cited

U.S. PATENT DOCUMENTS

| | | | |
|---|---|---|---|
| 5,589,154 | A | 12/1996 | Anderson |
| 5,595,743 | A | 1/1997 | Wu |
| 2001/0055630 | A1 | 12/2001 | Castillo et al. |
| 2002/0068098 | A1 | 6/2002 | Babish et al. |
| 2003/0180395 | A1 | 9/2003 | Bueter |
| 2004/0247698 | A1 | 12/2004 | Valenzuela Cortes |
| 2005/0064048 | A1 | 3/2005 | Li et al. |
| 2008/0070826 | A1 | 3/2008 | Selby, III |
| 2008/0260704 | A1 | 10/2008 | Riordan et al. |
| 2009/0022827 | A1 | 1/2009 | Li et al. |

FOREIGN PATENT DOCUMENTS

| | | |
|---|---|---|
| CN | 1069629 | 3/1993 |
| CN | 1176814 | 3/1998 |
| CN | 1279970 | 1/2001 |
| CN | 1437973 | 8/2003 |
| CN | 1515311 | 7/2004 |
| CN | 1558769 | 12/2004 |
| CN | 1682788 | 10/2005 |
| CN | 1708313 | 12/2005 |
| CN | 101040901 | 9/2007 |
| CN | 101091751 | 12/2007 |
| CN | 101099770 | 1/2008 |
| CN | 101125171 | 2/2008 |
| CN | 101274012 | 10/2008 |
| CN | 101406537 | 4/2009 |
| JP | 2002-255804 | 9/2002 |
| JP | 2003-201229 | 7/2003 |
| JP | 2003342190 A * | 12/2003 |
| JP | 2006-347967 | 12/2006 |
| JP | 2007-204447 | 8/2007 |
| JP | 2007-217352 | 8/2007 |
| JP | 2008-007417 | 1/2008 |
| JP | 2008-074801 | 4/2008 |
| KR | 100718602 | 5/2007 |
| KR | 20090020279 | 2/2009 |
| WO | WO-02/09720 | 2/2002 |
| WO | WO-02/078685 | 10/2002 |
| WO | WO-03/043645 | 5/2003 |
| WO | WO-2004/052381 | 6/2004 |
| WO | WO-2005/034958 | 4/2005 |
| WO | WO-2006/054370 | 5/2006 |
| WO | WO-2007/048352 | 5/2007 |
| WO | WO-2007/048353 | 5/2007 |
| WO | WO-2007/049088 | 5/2007 |
| WO | WO-2007/049089 | 5/2007 |
| WO | WO-2007/106049 | 9/2007 |
| WO | WO-2008/144706 | 11/2008 |
| WO | WO-2010/143058 | 12/2010 |
| WO | WO-2010/143059 | 12/2010 |
| WO | WO-2010/143061 | 12/2010 |
| WO | WO-2010/143062 | 12/2010 |
| WO | WO-2010/143063 | 12/2010 |
| WO | WO-2010/143065 | 12/2010 |

OTHER PUBLICATIONS

Euficreview. Web Publication date:Nov. 1998 [Retrieved from the Internet on: Mar. 25, 2013]. Retrieved from: <URL: http://www.eufic.org/article/en/expid/review-diet-lifestyle-life-expectancy/>.*

(Continued)

*Primary Examiner* — Amy L Clark
(74) *Attorney, Agent, or Firm* — Foley & Lardner LLP

(57) ABSTRACT

Disclosed herein are compounds, extracts, and active fractions of the plant *Geum japonicum* and methods for increasing longevity and survival potency or for preventing or treating various medical conditions, including diabetes, inflammation, wound healing, bed sores, and ocular disorders. The compounds provided herein can be formulated into pharmaceutical compositions and medicaments that are useful in the disclosed methods. Also provided are the use of the compounds and extracts in preparing pharmaceutical formulations and medicaments.

6 Claims, 4 Drawing Sheets

(56) References Cited

OTHER PUBLICATIONS

Extended Search Report issued in European Application No. 10785823.5 dated Nov. 8, 2012 (12 pages).
Extended Search Report received in European Application No. 10785819.3 dated Nov. 8, 2012 (10 pages).
Extended Search Report received in European Application No. 10785820.1 dated Nov. 13, 2012(7 pages).
Extended Search Report received in European Application No. 10785822.7 dated Nov. 8, 2012(9 pages).
International Preliminary Report on Patentability issued for PCT/IB2010/001418 mailed Nov. 22, 2012 (7 pages).
Kang, Soon Ah et al., "Antiinflammatory Activity of the Medicinal Plant Geum Japonicum," Nutritional Sciences, vol. 9, No. 2, (May 1, 2006), pp. 117-123.
Li, Ming et al., "Repair of Infarcted Myocardium by an Extract of Geum japonicum with Dual Effects on Angiogenesis and Myogenesis," Clinical Chemistry, vol. 52, No. 8, (Aug. 1, 2006), pp. 1460-1468.
Myeong-Sim, Ji et al., "Anticoagulant 1,2,3,4,6-pentagalloyl-beta-D-glucopyranos e isolated from geranium (*Pelargonium inquinans* Ait)," Archives of Pharmacal Research, vol. 28, No. 9, (Sep. 2005), pp. 1037-1041.
Non-Final Office Action received in U.S. Appl. No. 13/377,489 dated Nov. 21, 2012 (9 pages).
Samuels, Noah, "Herbal remedies and anticoagulant therapy," Thrombosis and Haemostasis, vol. 93, No. 1 (Jan. 1, 2005), pp. 3-7.
Somova, Lo et al., "Cardiovascular, Antihyperlipidemic and Antioxidant Effects of Oleanolic and Ursolic Acids in Experimental Hypertension," Phytomedicine, vol. 10, No. 2-3, (Jan. 1, 2003), pp. 115-121.
Xie, Yi-Wu et al., "Role of Nitric Oxide in the Vasorelaxant and Hypotensive Effects of Extracts and Purified Tannins from Geum Japonicum," Journal of Ethnopharmacology, vol. 109, (2007), pp. 128-133.
Dong, H., et al., "Effects of Tannins from Geum japonicum on the Catalytic Activity of Thrombin and Factor Xa of Blood Coagulation Cascade," J. Nat. Prod., Oct. 1998, vol. 61, No. 11, pp. 1356-1360.
International Preliminary Report on Patentability received for PCT/IB2010/001410 mailed Dec. 12, 2011.
International Preliminary Report on Patentability received for PCT/IB2010/001412 mailed Dec. 12, 2011.
International Preliminary Report on Patentability received for PCT/IB2010/001415 mailed Dec. 12, 2011.
International Preliminary Report on Patentability received for PCT/IB2010/001416 mailed Dec. 12, 2011.
International Preliminary Report on Patentability received for PCT/IB2010/001418 mailed Dec. 12, 2011.
International Preliminary Report on Patentability received for PCT/IB2010/001426 mailed Dec. 12, 2011.
International Search Report received for PCT/IB2010/001415 mailed Oct. 21, 2010.
International Search Report received for PCT/IB2010/001410 mailed Nov. 11, 2010.
International Search Report received for PCT/IB2010/001412 mailed Nov. 11, 2010.
International Search Report received for PCT/IB2010/001416 mailed Nov. 11, 2010.
International Search Report received for PCT/IB2010/001418 mailed Nov. 11, 2010.
International Search Report received for PCT/IB2010/001426 mailed Nov. 11, 2010.
Li, J., "Studies on Bioactive Constituents with Myogenesis and Angiogenesis Activity from *Geum japonicum* Thunb" Vax. Chinese F. Bolle, Chinese Doctoral Dissertation & Master's Thesis, Medicine and Health Sciences, Jan. 2007, 41 pages. (English abstract provided).
Liu, H., et al., "Fatty Acid Synthase Inhibitors from Geum Japonicum Thunb. var. Chinese," Chemistry & Biodiversity, Mar. 24, 2009, vol. 6, Issue 3, pp. 402-410.

Ming, D.S., et al. "Research Progress in Chemical Constituents and Biological Activities of Geum Species," Acta Pharmaceutica Sinica, 2000, vol. 35, No. 7, pp. 552-558.
Yoshiki, K., et al. "Antitumor agents, 129.1 Tannins and Related Compounds as Selective Cytotoxic Agents," Journal of Natural Products, Aug. 1992, vol. 55, No. 8, pp. 1033-1043.
Zeng, F., et al., "The Anticoagulant Effects of Geum japonicum Extract and its Constituents," Phytotherapy Research, Mar. 1998, vol. 12, pp. 146-148.
Bhattachrya, Salil K. et al., "Effect of Bioactive Tan noid Principles of Emblica Officinalis on Ischemia-Reperfusion-Induced Oxidative Stress in Rat Heart," Phytomedicine, vol. 9, No. 2, Jan. 1, 2002, pp. 171-174.
Fogo, A.S et al., "Tormentic acid reduces vascular smooth muscle cell proliferation and survival," European Journal of Pharmacology, vol. 615, No. 1-3, Aug. 1, 2009, pp. 50-54.
Search Report issued in European Application No. 10785821.9 dated Feb. 15, 2013 (10 pages).
Search Report received in European Application No. 10785818.5 dated Feb. 19, 2013 (11 pages).
Final Office Action issued in U.S. Appl. No. 13/377,489 mailed May 22, 2013 (16 pages).
NDIC, "Diagnosis of Diabetes", Internet Archive Date: Feb. 28, 2005 [Retrieved from internet on: May 18, 2013 by USPTO Examiner]. Retrieved from the Internet: <URL: http://web.archive.org/web/20050228073517/http://diabetes.niddk.nih.gov/dm/pubs/diagnosis/> (7 pages).
Yoshida, etal., "Tannins of Rosaceous Medicinal Plants. Part 2. Gemins A, B, and C, New Dimeric Ellagitannins from *Geum japonicum*", J. Chem. Soc. Perkin Trans. I, (1985), pp. 315-321.
Adams, K.F. et. al.,"Clinical benefits of low serum digoxin concentrations in heart failure," Jnl of Am College of Cardiology, (2002), vol. 39, No. 6, pp. 946-953.
Anderson, Koren J. et al., "Walnut Polyphenolics Inhibit in Vitro Human Plasma and LDL Oxication 1,2," Jnl of Nutrition, (2001), 131(11), pp. 2837-2842.
Bonfill, M. et al., "Identification of triterpenoid compounds of Centella asiatica by thin- layer chromatography and mass spectrometry," Biomedical Chromatography, (2005), 20(2), pp. 151-153.
Brinkhaus, B. et al., "Chemical, pharmacological and clinical profile of the East Asian medical plan Centella aslatica," Phytomedicine, (2000), vol. 7(5), pp. 427-448.
Definitions of "Ischemic Heart Disease" and "Coronary Heart Disease" from Hyperdictionary, retreived on Sep. 11, 2013 from http://hyperdictionary.com.
Fukuda, Toshiyuki et al., "Antioxidative polyphenols from walnuts (*Juglans regia* L.)," Phytochemistry, (2003), 63(7), pp. 795-801.
Lapornik, Brigita et al., "Comparison of extracts prepared from plant by-products using different solvents and extraction time," (2005), Jnl Food Engineering, 71(2), pp. 214-222.
Larrosa, Mar et al., "Ellagitannins, ellagic acid and vascular health," Molecular Aspects of Medicine, (2010), 31(6), pp. 513-539.
Meredith, Peter A. et al., "From Hypertension to Heart Failure-Are there better primary prevention strategies?," Jnl of Renin-Angiotension-Aldosterone System, (Jun. 2006), vol. 7, No. 2, pp. 64-73.
Non-Final Office Action issued in U.S. Appl. No. 13/377,483 mailed Aug. 22, 2013 (27 pages).
Non-Final Office Action issued in U.S. Appl. No. 13/377,503 mailed Aug. 30, 2013 (28 pages).
Pragada, R.R. et al., "Carioprotective activity of *Hydrocotyle asiatica* L. In ischemia-reperfusion induced myocardial infarction in rats," Jnl of Ethnopharmacology, (2004), 93, pp. 105-108.
Turkmen, Nihal et al., "Effects of extraction solvents on concentration and antioxidant activity of black and black mate tea polyphenols determined by ferrous tartrate and Folin-Ciocalteu methods," (2006), Food Chemistry, 99(4), pp. 835-841.
Wojtczak, Dr. Andrzej, "Glossary of Medical Education Terms: 'Prevention'," (Feb. 2002), 5 pages.
Yoshida, Takashi et al., "Dimeric ellagitannins, laevigatins E, F and G from Rosa Laevigata," Phytochemistry, (1989), vol. 28, No. 9, pp. 2451-2454.
Final Office Action received in U.S. Appl. No. 13/377,483 mailed Mar. 28, 2014 (24 pages).

(56) References Cited

OTHER PUBLICATIONS

Final Office Action received in U.S. Appl. No. 13/377,503 mailed Apr. 2, 2014 (18 pages).
Examination Report No. 1 received in Australian Patent Application No. 2010258358 issued Oct. 15, 2014, 5 pages.
Bhattacharya, Salil K. et al., "Effect of bioactive tannoid principles of Emblica officinalis on ischemia-reperfusion-induced oxidative stress in rat heart," Phytomedicine, (2002), vol. 9, pp. 171-174.
Dong-Sheng, Ming et al., "Research Progress in Chemical Constituents and Biological Activities of Geum Species," Acta Pharma, (2000), vol. 35, No. 7, pp. 552-558.
Office action received in Japanese Patent Application No. 2012-514548 issued Jun. 16, 2014, 7 pages, with English translation.
Office Action received in Japanese Patent Application No. 2012-514549 issued Jul. 2, 2014, 5 pages with English translation.
Office Action received in Japanese Patent Application No. 2012-514550 issued May 21, 2014, 6 pages with English translation.
Office Action received in Japanese Patent Application No. 2012-514551 issued Jun. 30, 2014, 9 pages with English translation.
Office Action received in Japanese Patent Application No. 2012-514552 issued May 26, 2014, 6 pages, with English translation.
Office Action received in Japanese Patent Application No. 2012-514554 issued May 28, 2014, 8 pages, with English Translation.
Patent Examination Report No. 1 received in Australian Patent Application No. 2010258351 issued Jul. 31, 2014, 4 pages.
Patent Examination Report No. 1 received in Australian Patent Application No. 2010258352 issued Jul. 7, 2014, 4 pages.
Patent Examination Report No. 1 received in Australian Patent Application No. 2010258354 issued Jul. 11, 2014, 3 pages.
Patent Examination Report No. 1 received in Australian Patent Application No. 2010258355 issued Jul. 31, 2014, 3 pages.
Examination Report No. 2 on Australian Application 2010258354, issued Apr. 1, 2015.
Examination Report on Australian Application 2010258356, issued Apr. 2, 2015.
H.B. MacPhillamy: Drugs From Plants: Plant Science Bulletin, Botanical Society of America, vol. 9, No. 2, Apr. 1963, 15 pages.
MayoClinic: Alzheimer's Disease, from www.mayoclinic.com/health/alzheimers-diseas/DS00161/Method print&Dsection all, Jan. 28, 2013, 15 pages.
Non-Final Office Action on U.S. Appl. No. 13/377498, mailed Apr. 13, 2015.
Non-Final Office Action on U.S. Appl. No. 13/377502, mailed Apr. 7, 2015.
Phillipson, J. "New Drugs From Nature—It Could Be Yew," Phytiotherapy Research, 13, 1999, pp. 2-8.
Raskin et al., "Can an Apple a Day Keep the Doctor Away?" Current Pharmaceutical Design, 2004, 10, pp. 3419-3429.
Revilla et al., "Comparison of Several Procedures Used for the Extraction of Anthocyanins from Red Grapes, "J. Agric. Food Chem, 46, Oct. 29, 1998, pp. 3419-3429.
Smet et al., Herbal Remedies, The New England Journal of Medicine; vol. 347, Issue 25, Dec. 19, 2002, pp. 2046-2056.
Vickers et al., "A Vaccine Against Alzheimer's Disease,:" Drugs Aging, 19 (7), 2002, pp. 487-494.
Ansel, Howard C. et al., Seventh Edition, Pharmaceutical Dosage Forms and Drug Delivery Systems, "Chapter 2: New Drug Development and Approval Process," (1999), 6 pages.
Non-Final Office Action received in U.S. Appl. No. 13/377,503 mailed Jan. 6, 2015, 28 pages.
Non-Final Office Action received in U.S. Appl. No. 13/377,489 mailed Jan. 5, 2015, 21 pages.
Final Rejection on Japanese Application 2012-514550, mailed Feb. 2, 2015 (English translation included).
Lobmeyer et al., "Synergistic polymorphisms of Beta 1 and x2c-adrenegic receptors and the influence on left ventricular ejection fraction response to beta-blocker therapy in heart failure," Pharmacogenetics and genomics, 17, 2007, pp. 277-282.

Notice of Allowance on U.S. Appl. No. 13/377,483, mailed Feb. 11, 2015.
Office Action on Japanese Application 2012-514551, mailed Feb. 23, 2015, English translation provided.
Office Action on Japanese Application 2012-514554, mailed Feb. 25, 2015, English translation provided.
Office Action on Japanese Application 2012-514549, mailed Feb. 23, 2015, English translation provided.
Final Office Action on U.S. Appl. No. 13/377,503, mailed Jun. 29, 2015.
Final Office Action on U.S. Appl. No. 13/377,489, mailed Jul. 24, 2015.
Notice of Acceptance issued on Australian Application 2010258354, mailed Jul. 29, 2015.
Second Examination Report issued on Australian Application 2010258355, issued Aug. 5, 2015.
Non-Final Office Action on U.S. Appl. No. 13/377,503 mailed Jul. 14, 2016.
Office Action issued on Japanese Application 2015-111092, mailed Apr. 7, 2016 (English translation not available).
Zeng et al., "The Anticoagulant Effects of Geum japonicum Extract and its Constituents," Phytotherapy Research, vol. 12, 146-148, 1998.
Final Office Action on U.S. Appl. No. 13/377,502 mailed Feb. 22, 2016.
Medline Plus, National Institutes of Health/U.S.. National Library of Medicine, Degenerative Nerve Diseases, https://www.nlm.nih.gov/medlineplus/degeenrativenervediseases.html 2015.
National Institute of Neurological Disorders and Stroke NINDS Kuru Information Page, http://www.ninds.hih.gov/disorders/kuru/kuru.htm, 2015.
Office Action issued on Japanese Application 2012-514549, mailed Jun. 16, 2016, English translation only.
Office Action issued on Japanese Application 2015-126506, mailed Nov. 30, 2016.
Herrera et al, Functional Properties of Pentacylic Triterpenes Contained in "Orujo" Olive Oil, Current Nutrition & Food Science, 2006, pp. 45-49.
Kang et al., Anti-inflammatory Activity of the Medicinal Plant Geum Japonicum, Nutritional Sciences 9(2), May, 2006, pp. 117-123.
Rodriguez-Rodriguez et al., "Triterpenic Compounds from "orujo" Olive Oil Elicite Vasorelation in Aorta from Spontaneously Hypertensive Rats," Journal of Agricultural and Food Chemistry, 2006, pp. 2096-2102.
Final Office Action on U.S. Appl. No. 13/377,498 mailed Jan. 20, 2016.
Communication issued on EP Application 10785821.9, mailed Mar. 2, 2016.
Examination Report issued on EP Application 10785823.5, mailed Feb. 11, 2016.
Examination Report issued on EP Communication 10785822.7, mailed Feb. 11, 2016.
Examination Report issued on European Application 10785820.1, mailed Feb. 11, 2016.
Dubey et al., "Individuals at Risk of Coronary Heart Disease (CHD), its Prevention and Management by an Indigenous Compound," Ancient Science of Life, vol. No. XX (1&2), Jul.-Oct. 2000, p. 48-57.
Examination Report issued on European Application 10785818.5, mailed Dec. 2, 2016.
Gnanapragasam et al., "Protective effect of Centella asiaticaon antioxidant tissue defense system against Adriamycin inducted cardiomyopathy in rats," Life Sciences 76, 2004, pp. 585-597.
Non-Final Office Action on U.S. Appl. No. 13/377,498 mailed Feb. 8, 2017.
Office Action issued on Japanese application 2015-126332, mailed Dec. 19, 2016.

* cited by examiner

COMPOSITIONS AND METHODS FOR INCREASING LIFESPAN AND HEALTH SPAN

CROSS-REFERENCE TO RELATED APPLICATIONS

The present application is the U.S. National Stage Application of PCT International Application No. PCT/IB2010/001426, filed Jun. 11, 2010, which claims priority to U.S. Provisional Application No. 61/186,709, filed Jun. 12, 2009, and U.S. Provisional Application No. 61/187,905, filed Jun. 17, 2009, the entire contents of which are hereby incorporated by reference in their entirety.

BACKGROUND

The following description is provided to assist the understanding of the reader. None of the information provided or references cited is admitted to be prior art to the present invention.

Longevity has long been one of the hottest areas of science, but it remains a poorly understood area of research. Critically and scientifically speaking, people do not know how to measure aging. Aging is not merely chronological. Some people are spry and nimble in their elder years, while others are afflicted by the diseases of aging—heart disease, hypertension, stroke, diabetes, cancer, Alzheimer disease, and dementia—by middle age.

It is a consensus that the population almost everywhere of the world is graying rapidly. The percentage of people age 65 and older is increasing from 7% in 2005 to 16% in 2050. The number of elderly people has already tripled since 1950, and will triple again by 2050, when 1.5 billion people will be over 65. Aging research involving the search for single-gene mutations with dominant positive effects on lifespan/health span has not been successful. Aging is a generalized degenerative deterioration, and is probably not due to changes in a single gene or system.

The phenomenon of limited cellular division was first observed by Leonard Hayflick, which is now referred to as Hayflick limit. During cell division, the replication of DNA cannot proceed all the way to the end of the chromosome. A telomere is a region of repetitive DNA at the end of a chromosome, which protects the end of the chromosome from deterioration. Without telomeres, cells would lose the ends of their chromosomes, and the necessary information they contain during their replication. The telomeres act as a disposable buffer blocking the ends of chromosomes that are consumed during cell division and replenished by an enzyme, the telomerase. Telomerase is capable of replenishing the 3' end of chromosomes by adding TTAGGG repeats (Autexier C et al. 2006, Collins K et al. 2006).

Lengthening telomeres in certain important cells through temporary activation of telomerase, or by gene therapy for life extension has long been proposed. A study done with the nematode worm species *Caenorhabditis elegans* indicates that there is a correlation between lengthening telomeres and a longer lifespan. The worms with longer telomeres lived 24 days on average, about 20 percent longer than the normal worms (Artandi S E et al. 2000).

SUMMARY

The present invention relates inter alia to an organic extract of *Geum japonicum* (OEGJ) that enhances the longevity of cells in cell culture systems. The present inventors surprisingly found that the cells in culture and tissues from experimental animals that were treated with OEGJ showed significantly increased telomerase activity. Further studies of OEGJ in animal models demonstrated an increased lifespan. Without wishing to be limited by theory, the up-regulation of survival-enhancing genes, such as Atk1, Bcl2, VEGF and NFκB, and telomerase activity are the underlying mechanisms for the enhanced survival and longevity of the experimental animals.

In some embodiments, the invention relates to the use of a pharmaceutical composition and a method of enhancing longevity and revitalization. Particularly, it relates to a pharmaceutical composition and method for enhancing the vitality and stimulating the activity of telomerase in mammalian subjects so that it can be used for anti-aging and substantial enhancement of a healthy lifespan and longevity.

In one aspect, the present disclosure provides a method for enhancing longevity and quality of life in a subject in need thereof, the method comprising administering to the subject an effective amount of OEGJ. In one embodiment, the administration of the extract stimulates expression of telomerase and one or more cell survival factors selected from the group consisting of Akt1, Bcl2, EGF, VEGF and NFκB. In one embodiment, the administration of the extract increases lifespan or quality of life compared to a subject not administered the extract. In one embodiment, the subject is a human.

In one embodiment, the organic extract is an ethanol extract. In one embodiment, the organic extract is a methanol extract. In one embodiment, the extract is administered orally. In one embodiment, the extract is administered by subcutaneous injection, intramuscular injection, or intravenous infusion. In one embodiment, the extract is administered in an amount of from 0.01 mg/kg/day to 10000 mg/kg/day. In one embodiment, the effective amount of the extract is in the form of a pharmaceutical formulation comprising the extract and a suitable carrier or excipient therefor.

In another aspect, the present disclosure provides a pharmaceutical composition for enhancing longevity and quality of life in a subject comprising an effective amount of OEGJ and a pharmaceutically acceptable carrier.

In another aspect, the present disclosure provides a method for preventing or treating diabetes in a subject in need thereof, the method comprising administering to the subject an effective amount of OEGJ.

In another aspect, the present disclosure provides a method for preventing or treating ocular diseases or conditions in a subject in need thereof, the method comprising administering to the subject an effective amount of OEGJ.

In another aspect, the present disclosure provides a method for treating inflammation in a subject in need thereof, the method comprising administering to the subject an effective amount of OEGJ.

In another aspect, the present disclosure provides a method for enhancing wound healing in a subject having a wound, the method comprising administering to the subject an effective amount of OEGJ. In one embodiment, the wound is a bed sore.

DETAILED DESCRIPTION

Figure 1:
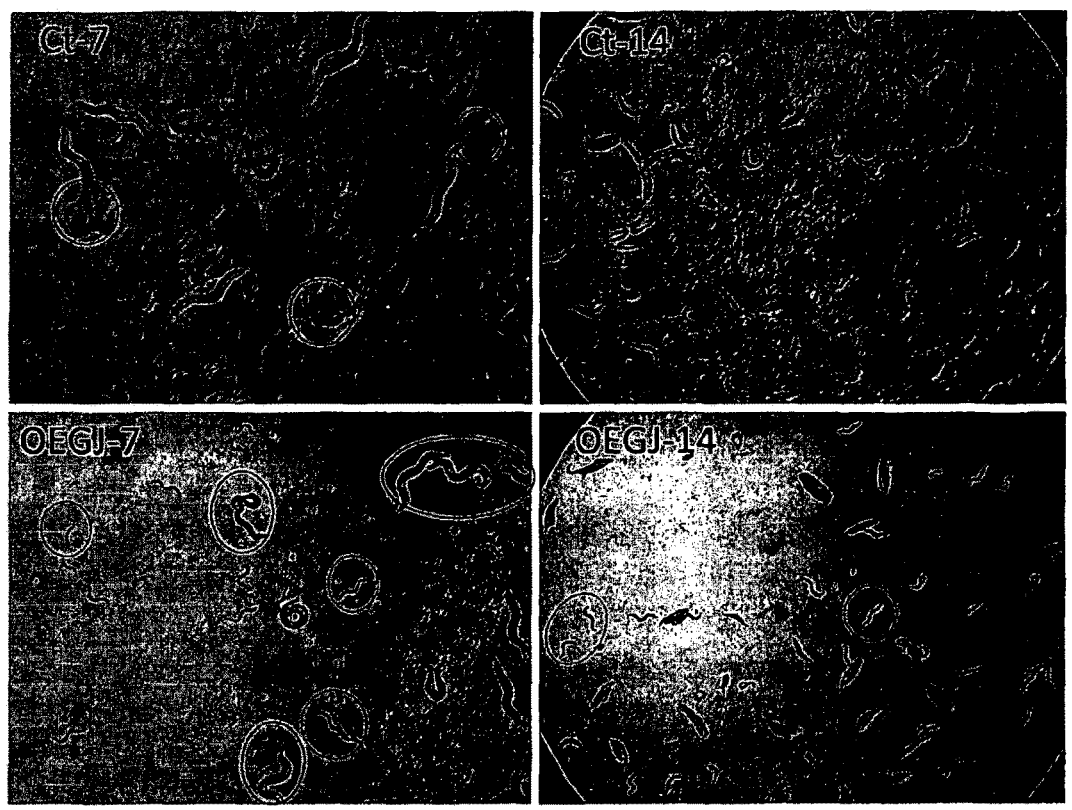
FIG. 1 shows that OEGJ enhanced survival potency or life expectancy in *C. elegans*. Wild type N2 *C. elegans* were grown on NGM agar plates streaked with *Escherichia coli* strain OP50 in forced-air incubators. The N2 worms at L1 in the test group were treated with OEGJ (150 μg/ml) and the worms in control group were treated with equivalent solvent. In order to test the survival potency of the OEGJ treated worms, the culture temperature was increased up to 27° C. Ct-7, the N2 worms in non-treated control group at 27° C. for 7 days, some of the worms died with some of them still alive, but no young worms were observed. OEGJ-7, OEGJ-treated worms at the same condition for 7 days, almost no worms died and interestingly many young worms were observed. Ct-14, after 14 days incubation at 27° C., all N2 worms in non-treated control group died. OEGJ-14, although, after 14 days incubation at 27° C., most of the adult worms died, many young worms were observed still alive in OEGJ treated samples.

In various aspects, the present invention provides compounds, extracts, and methods for increasing longevity and for preventing or treating various medical conditions. The compounds provided herein can be formulated into pharmaceutical compositions and medicaments that are useful in the disclosed methods. Also provided are the use of the compounds and extracts in preparing pharmaceutical formulations and medicaments.

It is to be appreciated that certain aspects, modes, embodiments, variations and features of the invention are described below in various levels of detail in order to provide a substantial understanding of the present invention. The following terms are used throughout as described below, unless context clearly indicates otherwise.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

The abbreviation "OEGJ" used in the invention, without specific indication, means an extract of the plant *Geum japonicum* by an organic solvent described below.

As used herein, the term "longevity" refers to the lifespan of the animal. Thus, longevity refers to the number of years in the lifespan of an animal. In some embodiments, the term "increased longevity" with regard to subjects administered the compositions of the invention, means that the lifespan of a non-diseased animal administered the compositions is increased relative to another non-diseased animal not administered the compositions. In some embodiments, the longevity of the animal is increased at least 6 months, at least 1 year, at least two years, at least 3 years, at least 4 years, at least 5 years, or at least 10 years compared to a non-diseased animal not administered the compositions. In some embodiments the longevity of the animal is increased at least one year, but not more than 10 years, not more than 5 years, or not more than 4 years compared to a non-diseased animal not administered the compositions.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the term "subject" refers to a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

Compositions of the Invention

The present invention provides methods increasing longevity in a subject with extracts and compounds, and derivatives of such compounds from a variety of plants including *Geum japonicum* and Xian he cao (also known as *Agrimonia pilosa* Ledeb.

In some embodiments, the compound is a whole plant, an extract, e.g., an organic extract, of *Geum japonicum* or Xian he cao. In a particular embodiment, the compound is a methanol/ethanol extract of *Geum japonicum* or an active fraction thereof. In some embodiments, the compound is a fraction of an extract of *Geum japonicum*.

The present invention provides methods of increasing longevity in a subject with agents and/or extracts and compounds, and derivatives of such compounds from a variety of plants including *Geum japonicum*. In some embodiments, the agent is an extract, e.g., an organic extract, of *Geum japonicum*. In a particular embodiment, the agent is a methanol/ethanol extract of *Geum japonicum* or an active fraction thereof.

Preparation of Organic Extract of *Geum japonicum*

A method for preparing an organic extract from *Geum Japonicum* Thunb var is provided. This method comprises the step of (a) extracting the plant of *Geum Japonicum* Thunb with alcohol selected from the group consisting of C1-C4 alcohols. This step maybe repeated 3-6 times, typically 5 times, at room temperature. Before performing step (a), the plant material may be powdered or cut into small pieces. The C1-C4 alcohols include methanol, ethanol, n-propanol, iso-propanol, n-butanol, iso-butanol, and ter-butanol. Typically, alcohol is added in 1-10 times by weight of the amount of the *Geum Japonicum* thunb var. to be extracted.

The methods may further comprise the step of (b) drying the extract obtained from the step of (a) into a dried powder; and (c) successively extracting the powder obtained from the step of (b) with C6 alkane, EtOAc and an alcohol selected from the group consisting of C1-C4 alcohols. The C6 alkane includes cyclic and non-cyclic alkane having 6 carbon atoms, including, for example, cyclohexane, n-hexane, and neo-hexane, etc. The C1-C4 alcohols include methanol, ethanol, n-propanol, iso-propanol, n-butanol, iso-butanol, and ter-butanol. The amount of organic solvent to be used is typically 1-10 times by weight of the amount of the powders to be further extracted.

The method as recited above may also include filtering the extract to remove any insoluble powders therein. A drying step may be completed under reduced pressure at a temperature higher than room temperature, for example, at 50° C.

To purify the OEGJ, the method may further comprise the steps of applying the powder to a chromatographic column; and eluting the column with an aqueous solution with increasing concentration of an alcohol selected from the group consisting of C1-C4 alcohols. For example, a Sephadex or reverse phase column may be used. The alcohol used may be any one selected from the group consisting of methanol, ethanol, n-propanol, iso-propanol, n-butanol, iso-butanol, and ter-butanol.

By NMR analysis, it is found that the OEGJ typically contains mainly tannins including gemin A, B, C, D, E and F and triterpenes including 2-hydroxyoleanonic acid, 2-hydroxyursolic acid, 2,19-dihydroxy-ursolic acid, 2-α, 19-α-dihydroxy-3-oxo-12-ursen-28-oic acid, ursolic acid, epimolic acid, maslinic acid, euscaphic acid, tormentic acid, 28-β-D-glucoside of tormentic acid.

In one embodiment, the extracts, fractions, and compounds of the invention are obtained by extraction, using water and/or of an organic solvent, from crude plant material comprises the following stages:

1. Extraction by addition to the plant material, of water and/or of organic solvent(s), by subjecting the whole to a treatment such as maceration/lixiviation, ultrasonics or microwaves;
2. Dilapidation before or after the extraction stage using a solvent of petroleum ether, hexane or chloroform type;
3. Optionally, additional extraction of the extract recovered by an organic solvent of ethyl acetate or ethyl ether type,
4. Optionally, concentration of the crude extract obtained, and, if desired, its lyophilization.

According one aspect, considering the enrichment that it allows to be attained, the crude extract may be subjected to a purification stage by chromatography. In one embodiment, centrifugal partition chromatography (CPC) is used. This technique is in particular described by A. P. FOUCAULT, Ed., Centrifugal Partition Chromatography, Chromatographic Science Series, Marcel Dekker Inc., 1995, 68, or W. D. CONWAY, Ed., Countercurrent Chromatography apparatus theory and applications, VCH Publishers Inc., 1990. CPC is based on the partition of the solutes between two non-miscible liquid phases prepared by the mixture of two or more solvents or solutions. One of the two phases is kept stationary by a centrifugal force. The solvents, their proportions and the flow rate chosen closely depend both on the stability of the stationary phase within the CPC column and the actual pressure.

A person skilled in the art will therefore choose the most appropriate solvent or solvents depending on the nature of the purified extract desired. Thus, crude extracts and enriched fractions are therefore available containing, as majority constituents, any of the identified compounds from OEGJ. These different extracts, namely crude or enriched also fall within the scope of the invention. The implementation of additional separation stages allows isolation of these extracts enriched with one or more compounds. These separations can be carried out on fractions enriched from a crude extract or on the crude extract itself by using mixtures of appropriate solvents according to the proportions which are suitable for the sought separation.

Methods and Compositions for Increasing Lifespan or Health Span

The present invention is based on the discovery that OEGJ not only enhanced the survival capacities of important cells, such as neurons and cardiac myocytes by protecting them from ischemia and stresses, but also up-regulated the expressions of cell survival factors, such as Akt1, Bcl2. EGF, VEGF, NFκB, and telomerase. Furthermore, the present inventors discovered that OEGJ can promote neovascularization in important ischemic organs, such as heart and brain and stimulate cardiac and neuronal regenerations in damaged hearts and brains. Given the positive implications derived from these experiments, OEGJ can effectively prevent or even reverse, in some degree, aging, and enhance lifespan or quality of life.

Generally, this invention relates to a method for improving age-related physiological disorders and extending lifespan in mammals as well as improving the quality of life of elderly mammals. In accordance with one aspect, the invention provides methods of increasing the longevity and/or enhancing the vitality in a subject in need thereof, which comprises administering to the subject an effective amount of a compound, composition, fraction or extract described herein. In some embodiments, a methanol/ethanol extract of *Geum japonicum*, its active fractions, and isolated compounds significantly increase the activity of telomerase in treated cells/tissues and remarkably increase the lifespan of mammalian subjects. Agents described herein can significantly increase the vitality and survival potency of new born mammalian subjects. The treated mammalian subjects are more active and appear significantly healthier. Life-threatening stress-bearing ability of treated mammalian subjects also significantly increases compared with the non-treated control subjects.

In one aspect, the methods for the increasing the longevity and/or enhancing the quality of life include administering to a mammal in need thereof agents, fractions, and/or extracts and compounds, and derivatives of such compounds from a variety of plants including *Geum japonicum* and Xian he cao.

In another aspect, an agent for increasing the longevity and/or enhancing the quality of life is part of a pharmaceutical composition containing one or more excipients, carriers, or fillers. In one embodiment, the pharmaceutical composition is packaged in unit dosage form. The unit dosage form is effective in inducing increasing the longevity and/or enhancing the vitality and survival potency in the subject.

In various embodiments of the invention, suitable in vitro or in vivo assays are performed to determine the effect of an agent (extracts, fractions, and compounds) of the invention and whether its administration is indicated for the increasing the longevity and/or increasing the quality of life of mammalian subjects. In some embodiments, in vitro models are used to assess the effects of an agent on a subject. Suitable models include, but are not limited to, a stress resistance assay in which *C. elegans* are exposed to a lethal temperature at 27° C. in addition to the test agent. The effects of the agent in mediating the stress resistance in the organisms are investigated and compared to suitable controls.

In some embodiments, in vivo models of longevity are used to assess the effects of an agent on a subject. Suitable models include a lifespan assay in which age synchronous *C. elegans* worms are prepared and grown on agar supplemented with the test agent. Another model is the short lifespan mouse in which a single klotho gene mutation results in multiple age-related disorders. The effects of the agent in mediating the age-related disorders in the animal subject are investigated and compared to suitable controls.

In one embodiment, the invention provides a method for increasing the resistance of a cell to stress, or preventing apoptosis of a cell, by contacting the cell with plant extracts, active fractions, and/or compounds of the invention.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with plants, extracts, active fractions, and/or compounds of the invention to keep the cells, or progeny thereof, in culture for longer periods of time. Such cells can also be used for transplantation into a subject, e.g., after ex vivo modification.

Diabetes

In another aspect, plants, extracts, active fractions, and/or compounds of the invention may be used for treating or preventing a metabolic disorder, such as insulin-resistance, a pre-diabetic state, type I and II diabetes, and/or complications thereof.

Diabetes refers to a metabolic disorder in which a person has a high blood sugar level, either because the body cannot produce enough insulin or has a decreased ability to utilize insulin. Insulin, produced in the pancreas, is a hormone that converts glucose into energy at the cellular level. Glucose is essential to our health since it is the main form of energy for cells in the muscle and other tissues. However, abnormal high level of glucose in the blood, a condition also known as hyperglycemia, leads to acute and chronic vascular disease complications, such as blindness, kidney failure, coronary heart disease, stroke and amputations (Pankaj, 2007).

Type 1 and type 2 diabetes are the two most common forms of diabetes. Type 1 diabetes, most commonly found during childhood or adolescence, is primarily due to the loss of insulin-producing β-cells in islets of Langerhans in the pancreas that in turn results in insulin deficiency. A T-cell mediated autoimmune response against β-cells is the main underlying mechanism in type 1 diabetes. Type 2 diabetes, which accounts for 90% of all the diabetes cases, is mainly resulted from insulin resistance and β-cell dysfunction (Lin & Sun, 2010). In opposite to type 1 diabetes, insulin levels in type 2 diabetes patients, especially in the early stage, are very high as the body attempts to compensate for insulin resistance. However, when the disease progresses, even the higher than normal insulin levels fail to keep the plasma glucose at the normal levels due to insulin resistance and increase hepatic glucose production. Along the course of the disease, decrease of insulin production, probably resulted from a progressive deterioration in β-cell function and accelerated β-cell apoptosis, further aggravate the disease condition (Wajchenberg B L, 2007).

Our recent studies have shown that OEGJ can significantly promote the growth of new blood vessels in the muscles, heart and brain. Both OEGJ-induced angiogenesis and muscle regeneration will enhance glucose assumption in the body leading to lower blood glucose level in diabetes patients. Moreover, if OEGJ-induced cell regeneration, found in heart, brain and muscle, also exists in the pancreas, OEGJ treatment could compensate for the loss of β-cells. Therefore, administration of a plants, extracts, fractions, and/or compounds described herein may provide effect treatments for diabetic patients.

In an exemplary embodiment, plants, extracts, active fractions, and/or compounds of the invention may be administered as a combination therapy for treating or preventing diabetes. For example, one or more plants, extracts, active fractions, and/or compounds of the invention may be administered in combination with one or more anti-diabetic agents. Exemplary anti-diabetic agents include, for example, an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a peroxisome proliferator-activated receptor-γ (PPAR-γ) ligand such as troglitazone, rosiglitazone, pioglitazone or GW-1929, a sulfonylurea, glipizide, glyburide, or chlorpropamide wherein the amounts of the first and second compounds result in a therapeutic effect. Other anti-diabetic agents include a glucosidase inhibitor, a glucagon-like peptide-1 (GLP-1), insulin, a PPAR α/.gamma. dual agonist, a meglitimide and an αP2 inhibitor. In an exemplary embodiment, an anti-diabetic agent may be a dipeptidyl peptidase IV (DP-IV or DPP-IV) inhibitor, such as, for example LAF237 from Novartis (NVP DPP728; 1-[[[2-[(5-cyanopyridin-2-yl)amino]ethyl]amino] acetyl]-2-cyano-(S)-pyrrol-idine) or MK-04301 from Merck (see e.g., Hughes et al., Biochemistry 38: 11597-603 (1999)).

Inflammatory Diseases, Wound Healing and Bedsores

In other aspects, plants, extracts, active fractions, and/or compounds of the invention can be used to treat or prevent a disease or disorder associated with inflammation. Plants, extracts, active fractions, and/or compounds of the invention may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

Inflammation is a complex biological process by which the body reacts to infection, injury or irritation (Medzhitov, 2008). Inflammation is a defensive mechanism to protect the body from various disease-causing foreign objects, such as bacteria, viruses and parasites. Although acute inflammation is a prerequisite for healing wound and infection, prolonged inflammation, also known as chronic inflammation, due to the inability of the immune system to get rid of foreign objects, could lead to a host of diseases including rheumatoid arthritis, atherosclerosis, asthma, and inflammatory bowel disease (Ku et al., 2009; Hamid & Tulic, 2009; Kaser et al., 2010). Recently, links between chronic inflammation and central nervous system diseases, cancer, and heart attacks have also been proposed (Kang & McGavern, 2009; Grivennikov et al., 2010). Chronic inflammatory diseases, afflicting millions of people worldwide, is hard to treat and there are still no drugs for cure. Many drugs used for treating chronic inflammatory diseases tend to have severe side-effects including stomach bleeding, diabetes and high blood pressure.

In certain embodiments, one or more plants, extracts, active fractions, and/or compounds of the invention may be taken alone or in combination with other compounds useful for treating or preventing inflammation. Exemplary anti-inflammatory agents include, for example, steroids (e.g., cortisol, cortisone, fludrocortisone, prednisone, 6α-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

Wound healing is an intricate and dynamic process after accidental injury or surgical intervention in which the body repairs itself and restores cellular structures and tissue layers. There are three phases of normal wound healing: the inflammatory phase, the proliferative phase, and the remodeling phase (Stadelmann et al., 1998). Agiogenesis, in the proliferative phase, is vital to wound healing. During angiogenesis, new blood vessels are formed by vascular endothelial cells.

Bedsores, also known as pressure sores or pressure ulcers, are lesions resulted from mostly unrelieved pressure (Bluestein D & Javaheri A, 2008). Although they can affect any part of the body, bedsores are found mostly in body portions over bony or cartilaginous areas such as knees, ankles and elbows, especially the skin on buttocks, hips and heels. People who are at high risk of developing bedsores are those who are paralyzed or those who are unable to change body positions without help. Bedsores could be fatal if not caught early and is one of the leading iatrogenic causes of death in developed countries. Bedsores develop when persistent pressure cuts off circulation to vulnerable parts of the body. The affected tissue dies eventually due to inadequate blood supply. Therefore, agents that can improve blood flow would be useful in treating bedsores.

Ocular Disorders

One aspect of the present invention is a method for inhibiting, reducing or otherwise treating ocular disorders, including cataracts and presbyopia by administering to a patient a therapeutic dosage of plant, extract, active fraction or compound of the invention, or a pharmaceutically acceptable salt, prodrug or a metabolic derivative thereof.

In some embodiments, OEGJ is effective in treating certain ocular disorders, especially age-related and degenerative ocular disorders, such as cataract and presbyopia. A cataract is an opaque or cloudy area in the lens of the eye. Depending on its size and location, cataract interferes with normal vision from slight opacity to complete blindness. Age-related cataract is the most common type of cataract and affect 60% in those aged 65 to 74 and 91% in those aged 75 to 85. According to the World Health Organization, age-related cataract is responsible for ~50% of blindness worldwide and is the leading cause of vision loss among people over 55 (Asbell et al., 2005). It is believed that denaturation and clustering of lens proteins are the underlying cause of cataracts. On the other hand, presbyopia is also an age-related eye condition where the crystalline lens of the eye loses its flexibility progressively, making it difficult to focus on close objects with age (Charman, 2008).

Another aspect of the invention is the treatment, including inhibition and prophylactic treatment, of age related ocular diseases include cataracts, presbyopia, and the like, by administering to the subject in need of such treatment a therapeutic dosage of a plant, extract, active fraction or compound of the invention.

In one embodiment, a combination drug regimen may include drugs or compounds for the treatment or prevention of ocular disorders or secondary conditions associated with these conditions. Thus, a combination drug regimen may include one or more plant, extract, active fraction or compound of the invention and one or more therapeutic agents for the treatment of an ocular disorder. For example, one or more plant, extract, active fraction or compound of the invention can be combined with an effective amount of one or more of an agent.

Formulations and Dosages of Pharmaceutical Compositions.

In various embodiments of the invention, suitable in vitro or in vivo assays are performed to determine the effect of an agent (extracts, fractions and compounds) of the invention and whether its administration is indicated for treatment of the affected disease or medical condition in a subject. Examples of these assays are described above in connection with a specific disease or medical treatment.

Typically, an effective amount of the compositions of the present invention, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 2,000 mg per kilogram body weight per day. An exemplary treatment regime entails administration once per day or once a week or once a month. The agent usually administered on multiple occasions. Intervals between single dosages can be daily, weekly, monthly or yearly. Alternatively, the agents can be administered as a sustained release formulation, in which case less frequent administration is required. Dosage and frequency vary depending on the half-life of the agent in the subject. The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patent can be administered a prophylactic regime.

Toxicity.

Suitably, an effective amount (e.g., dose) of an agent described herein will provide therapeutic benefit without causing substantial toxicity to the subject. Toxicity of the agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agent described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

According to the methods of the present invention, the agents can be incorporated into pharmaceutical compositions suitable for administration. In some embodiments, the pharmaceutical compositions may comprise purified or substantially purified extracts of *Geum japonicum* and a pharmaceutically-acceptable carrier in a form suitable for administration to a subject. In other embodiments, the pharmaceutical compositions may comprise Pharmaceutically-acceptable carriers are determined in part by the particular composition being administered, as well as by the particular method used to administer the composition. Accordingly, there is a wide variety of suitable formulations of pharmaceutical compositions for administering the compositions (see, e.g., *Remington's Pharmaceutical Sciences*, Mack Publishing Co., Easton, Pa. $18^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the agent are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the agent, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The agent named in this invention can be present in unsalified or unesterified form, or in salified and/or esterified form, and the naming of such agent is intended to include both the original (unsalified and unesterified) compound and its pharmaceutically-acceptable salts and esters. Also, certain agents named in this invention can be present in more than one stereoisomeric form, and the naming of such agent is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present invention.

Suitable examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the agent, use thereof in the compositions is contemplated. Supplementary active compounds can also be incorporated into the compositions.

A pharmaceutical composition of the invention is formulated to be compatible with its intended route of administration. The compositions of the present invention can be administered by parenteral, topical, intravenous, oral, subcutaneous, intraarterial, intradermal, transdermal, rectal, intracranial, intraperitoneal, intranasal; intramuscular route or as inhalants. The agent can optionally be administered in combination with other agents that are at least partly effective in treating various diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the agents in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the agents are prepared with carriers that will protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

EXAMPLES

The present technology is further illustrated by the following examples, which should not be construed as limiting in any way.

Example 1

Identification of Composition Comprised of Natural Compounds for Enhancing Survival Capacity and Telomerase Activity A bio-assay guided strategy was used for screening plant constituents to identify the composition of compounds enhancing the activity of telomerase. During the screening of the plant extract, an organic extract from *Geum japonicum* (OEGJ) was identified to significantly enhance the survival capacity and telomerase activity. Briefly, 10 kg dried *Geum japonicum* collected from Anhui Province was cut into small pieces, which was percolated with 90% methanol/ethanol (10× volume) at room temperature for 6 days. The extract was electro-sprayed to yield a brown powder.

When the extract (150 μg/ml) was applied to a mesenchymal stem cell culture, it was found that OEGJ treatment could promote the survival potency against stresses, such as hypoxia. RT-PCR analysis demonstrated that some of cell survival-associated genes, such as Akt1, Bcl2, VEGF, EGF and NFκB, were up-regulated. Therefore, the OEGJ was further tested in the following studies.

Example 2

Enhancement of Survival Potential of the Cultured Cardiac Myocytes

Cell function, including cell division, differentiation, aging and death, is controlled by a multitude of cell signaling pathways. The development of some diseases is also dependent upon these cell functions, especially on cell aging and cell death, the probability of which increases with age. For example, loss of cardiac myocytes by apoptosis leads to heart failure and down-regulation of anti-apoptotic (survival) signals or over-expression of pro-apoptotic signals is closely involved in disease development.

First, we tested whether the OEGJ could enhance the survival potential or prevent cell death in cultured cardiac myocytes. The cultured cardiac myocytes were subjected to hypoxia by incubation in an environmental chamber. The chamber oxygen concentration was maintained at 10 mmHg for 24 hours. It was shown that the OEGJ treatment from the start of hypoxia until the end of hypoxia significantly increased the expression of some survival factors, such as Akt1, Bcl2, EGF, VEGF, NFκB, and significantly prevented cell death against hypoxia compared with the non-treated control myocytes. The number of apoptotic cells increased with prolonged hypoxia in the non-treated control myocytes. By contrast, OEGJ treatment increased the survival potential of the cells and decreased the number of apoptotic cells ($P<0.01$).

Example 3

OEGJ Increased the Survival in *C. elegans*

To test whether the OEGJ would enhance the survival potency or life expectancy in *C. elegans*, wild type N2 *C. elegans* was used. The *C. elegans* were synchronized by bleaching and divided into two groups on agar plates. The plates were 60 mm top-coating dishes (about 10 ml media in solid form). The worms were grown on NGM agar plates streaked with *Escherichia coli* strain OP50 in forced-air incubators that maintain temperature to ±0.5° C. About 500 worms/dish were treated with OEGJ (150 μg/ml, 600 μl of the drug solution onto one dish each air dried in hood) and the worms in control group were treated with equivalent solvent. *C. elegans* strain N2 can induce dauer larva formation in wild-type strains of *C. elegans* between 20° C. and 25° C. Above 25° C. to 26° C. is a lethal temperature to *C. elegans*. In order to test the survival potency of the OEGJ-treated worms, the culture temperature was increased up to 27° C. Pictures were taken on day 7 & 14 (worms were exposed at 20° C. when taking pictures).

It was found that after incubation of the N2 worms in non-treated control group at 27° C. for 7 days, some of the worms died while some of them were still alive, but no young worms were observed (FIG. 1: Ct-7). By contrast, in OEGJ-treated worms incubated under the same conditions for 7 days, almost no worms died and more interestingly many young worms were observed (FIG. 1: OEGJ-7). Furthermore, after 14 days incubation at 27° C., all N2 worms in non-treated control group died (FIG. 1: Ct-14). In sharp comparison, although many of the adult worms died in the OEGJ treated group, quite many young worms were observed still alive (FIG. 1: OEGJ-14). These results indicated that the tough and lethal temperature environment not only sterilized the N2 worms, but also killed all worms within two weeks. By contrast, OEGJ treatment not only enhanced the survival potency of the worms at their lethal temperature environment, but also kept their ability to produce offspring.

OEGJ Increased the Mean Health Span in *C. elegans*.

To test whether the OEGJ stimulated up-regulation of cell survival associated genes and enhanced survival potency in worms, *C. elegans* of wild type N2, daf-2 and daf-16 mutants were synchronized by bleaching and divided into two groups on agar plates respectively. The daf-2 gene encodes an insulin-like receptor in the worm *C. elegans*. Mutations in daf-2 have been shown to double the lifespan of the worms (Jennie B. et al., 1995; J. Apfeld & C. Kenyon, 1998). The gene is known to regulate reproductive development, aging, resistance to oxidative stress, thermotolerance, resistance to hypoxia, and also resistance to bacterial pathogens (M. S Gami & C. A. Wolkow, 2006). The daf-2 is the only insulin/IGF-1-like receptor in the worm. Insulin/IGF-1-like signaling is conserved from worms to humans. The daf-2 acts to negatively regulate the fork-head transcription factor daf-16 through a phosphorylation cascade. Researches revealed that daf-16 is required for daf-2-dependent lifespan extension and dauer formation. When not phosphorylated, daf-16 is active and present in the nucleus. The daf-16 plays an important part in determining the rate of aging and average lifespan of the *C. elegans* and its close evolutionary cousins (S. T. Henderson & T. E. Johnson, 2001). The daf-16 is found in many other animals, including humans. The daf-16 is part of a group of genes that drive the biological processes involved in aging, immunity and responses to stresses.

The synchronized L1s of N2, daf-2 and daf-16 worms (about 500 worms/dish) at 15° C. were grown at 20° C. on NG agar plates streaked with *Escherichia coli* strain OP50 in forced-air incubators that maintain temperature to ±0.5° C. The worms of the test groups were treated with OEGJ (150 μg/ml, 600 μl of the drug solution onto one dish and each air dried in hood) and the worms in control groups were treated with equivalent solvent. Another exceptional experiment was to synchronize L1 of daf-2 at 20° C. and grow them at 20° C. as well.

Figure 2:
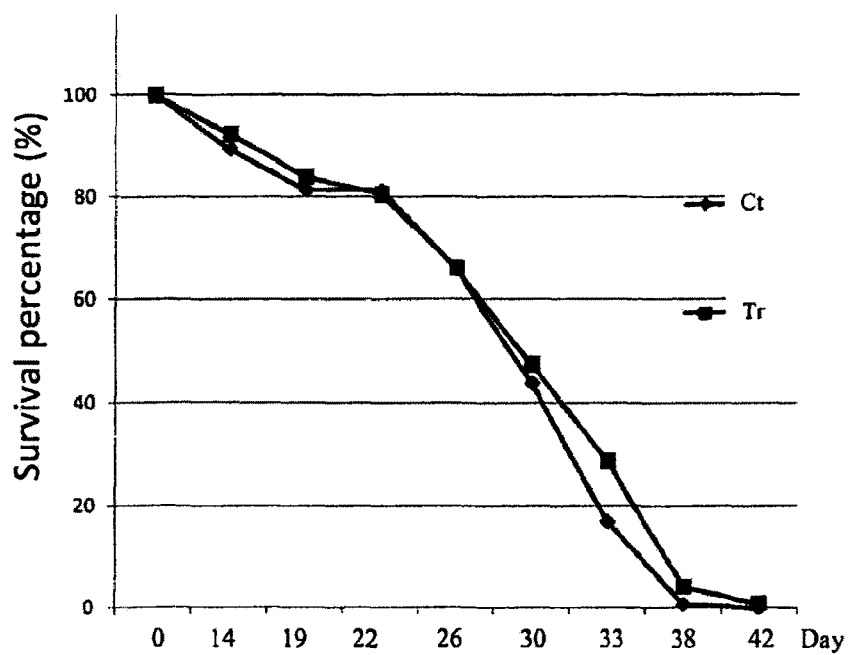
FIG. 2, The effect of OEGJ treatment on the lifespan/health span of N2 *C. elegans*. Ct, The non-treated control N2 worms. Tr, The OEGJ treated worms. It was shown that more live worms in OEGJ treated group were observed at almost all checking points than those of non-treated group. All worms of non-treated group died on day 38. However, about 5% of worms of OEGJ-treated group were still alive. The remaining worms of OEGJ-treated group died on day 42, about 10% longer than that of non-treated control worms.

As shown in FIG. 2, more live worms in the OEGJ-treated group were observed at almost all checking points compared to those of the non-treated group. All worms of the non-treated group died on day 38. However, about 5% of worms of OEGJ-treated group were still alive (FIG. 2). The remaining worms of OEGJ treated group died on day 42, and the average lifespan was about 10% longer than that of non-treated control worms.

Figure 3:
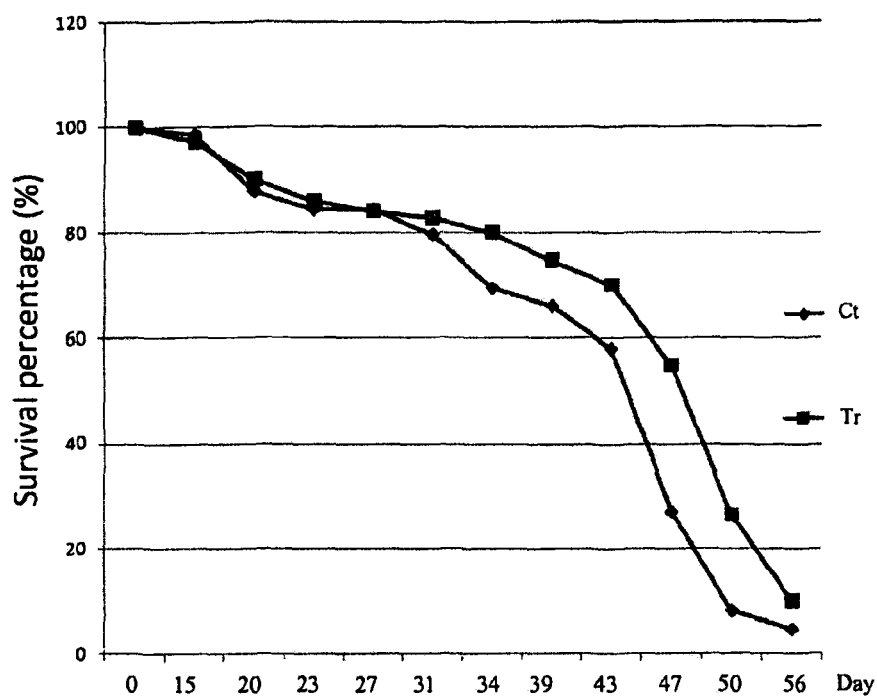
FIG. 3, The effect of OEGJ treatment on the lifespan/health span of daf-2 *C. elegans*. Ct, The non-treated control daf-2 worms. Tr, The OEGJ-treated worms. It was found that more live worms in OEGJ-treated group were observed at almost all observing points than those of non-treated group. Approximately 5% worms remained alive on day 56 in non-treated control group; however, about 10% of worms of OEGJ treated group were alive.

To test the effect of OEGJ treatment on the lifespan of daf-2 mutant C. elegans, which has an almost doubled lifespan than the wild type worms, daf-2 worms was tested with OEGJ. It was shown that more live worms in the OEGJ-treated group were found at almost all observing points compared to that of non-treated group (FIG. 3). Approximately 5% worms remained alive on day 56 in non-treated control, however, about 10% of worms of OEGJ-treated group were alive (FIG. 3).

Figure 4:
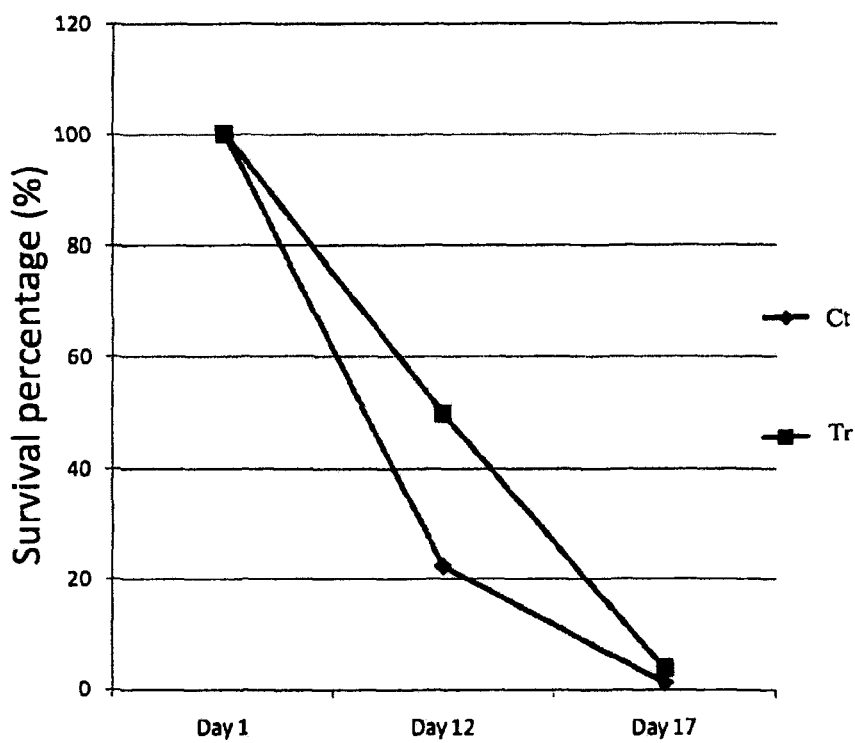
FIG. 4, The effect of OEGJ treatment on the lifespan/health span of daf-16 *C. elegans*. Ct, The non-treated control daf-16 worms. Tr, The OEGJ-treated daf-16 worms. Approximately 77% worms in non-treated control group died on day 12. By comparison, about 50% worms of OEGJ-treated group were found alive on day 12. Namely, approximately 27% more worms died in non-treated group than that of OEGJ-treated, indicating that the healthspan is significantly increased by OEGJ treatment.

To further test the effect of OEGJ treatment on the worms with significant shorter lifespan, daf-16 mutant C. elegans was used. It was found that about 77% worms in the non-treated control group died on day 12 (FIG. 4). By comparison, about 50% worms of the OEGJ treated group were found alive on day 12 (FIG. 4). About 27% more worms died in non-treated group than the OEGJ treated group, indicating the health span is significantly increased by OEGJ treatment.

Figure 5:
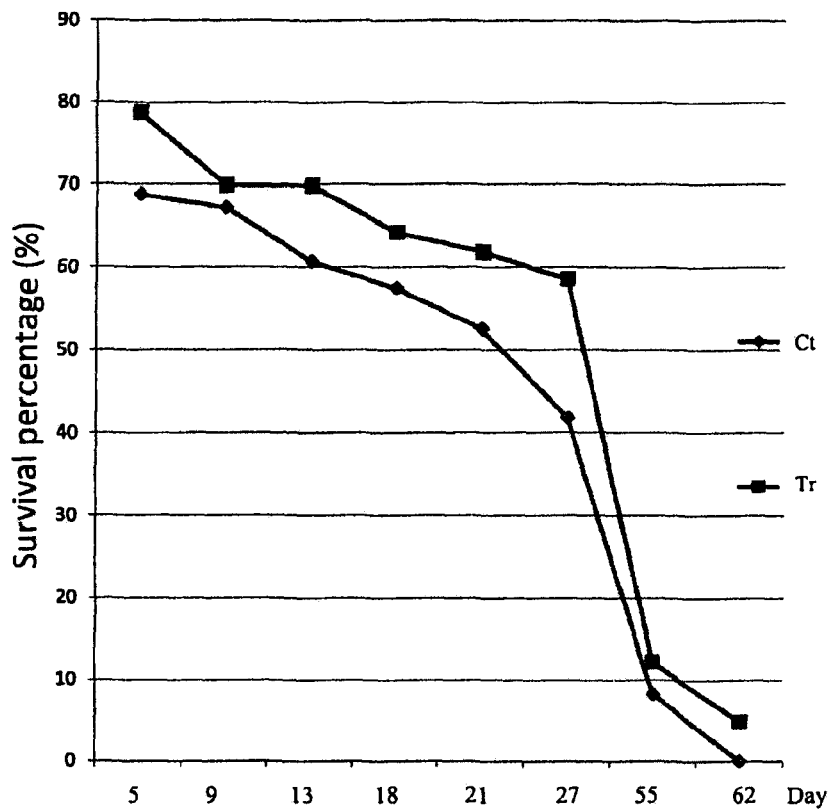
FIG. 5, The effect of OEGJ treatment on the lifespan/health span of daf-2 *C. elegans* synchronized L1 at 20° C. and grown at 20° C. Ct, The non-treated control daf-2 worms. Tr, The OEGJ-treated worms. About 58% of worms in OEGJ-treated group remained alive on day 21. By comparison, about 58% of worms in non-treated control group died on day 21. About 5-15% more worms in OEGJ-treated group were alive at all check points than those of non-treated control worms, indicating the increased health span and lifespan.

To still further test the effect of OEGJ treatment on the lifespan of daf-2 C. elegans in different conditions, the daf-2 worms were both synchronized and grown at 20° C. It was found that about 58% of worms in the OEGJ-treated group remained alive on day 21 (FIG. 5). By comparison, about 58% of worms in the non-treated control group died by day 21 (FIG. 5). About 5-15% more worms in OEGJ-treated group remained alive at all checking points, indicating the increased health span and lifespan.

Example 4

OEGJ-Treatment Induced Longevity and Increased Activity of Telomerase in Mice

The lifespan of Kunming (KM) mice is usually 582.5±177.73 days with normal feeding. KM mice (n=16) were randomly divided into two groups. The mice in test group (n=9, 6 months old) were given OEGJ (200 mg/kg/daily in their food) for two months. The mice in control group (n=7) at 6 months age were given sucrose (200 mg/kg/daily in their food) for the same period. Then the mice were housed in an environmentally controlled condition with a 12-h light/dark cycle. All animals had free access to standard rodent pellet food and water.

TERT (telomerase reverse transcriptase) is the catalytic subunit of telomerase. RT-PCR based on TaqMan® fluorescence methodology was used to quantify the full range of mTERT (mouse TERT) mRNA copy number. During the extension phase of the PCR, the probe hybridized to the target sequence and was then cleaved due to the 5' to 3' exonuclease activity of Taq polymerase. The increase in the fluorescence signal of the reporter was proportional to the amount of specific PCR products, providing highly accurate and reproducible quantification. The number of PCR cycles to reach the fluorescence threshold was the cycle threshold (Ct). The Ct value for each sample was proportional to the log of the initial amount of input cDNA. By plotting the Ct value of an unknown sample on the standard curve, the amount of target sequences in the sample could be calculated. To normalize the mTERT mRNA expression for sample-to-sample differences in RNA input, RNA quality, and reverse transcriptase efficiency, the housekeeping gene GAPDH was amplified. According to each standard curve, the copy numbers of GAPDH and mTERT, respectively, were determined. The ratio between copy numbers of mTERT and GAPDH represented the normalized mTERT for each sample and could be compared with that of other samples (Artandi S E et al. 2000).

Four mice from the OEGJ-treated group and two mice from non-treated control group were sacrificed after two months administration of OEGJ. The total RNA was prepared from heart using Trizol (Invitrogen) respectively. The GC1 cell line was used as the positive control for the experiment. Reverse transcription was performed with random hexamers with Superscript II (Invitrogen) following the manufacture's instructions. Real time PCR was performed for two dilutions in duplicates on a BioRad MJ Mini Real Time PCR. For each mRNA sample, Tert expression was corrected by the GAPDH mRNA content. The program was an initial incubation of 2 min at 50° C., followed by 10 min at 95° C. and 40 cycles of 15 s 95° C., 2 min 15 s 68° C., 15 s 95° C., 20 s 63° C., 15 s 95° C. In each cycle the melting point of the product was determined. The PCRs employed a set of primers specific for the Tert gene.

Figure 6:
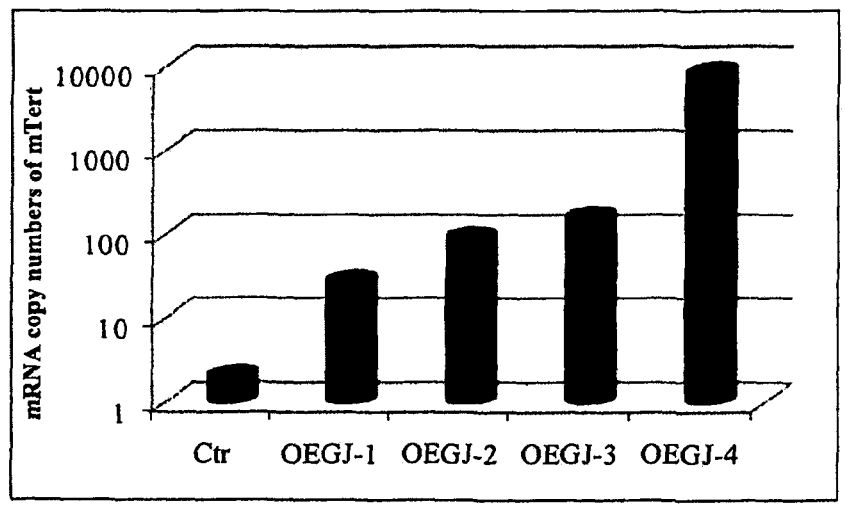
FIG. 6, OEGJ treatment induced up-regulation of mTERT expression in hearts. Ctr, mTERT signal from non-treated control hearts of mice. OEGJ-1-4, denotes the mTERT signals from OEGJ-treated hearts of mice. Positive signals of mTERT were observed in all four OEGJ-treated heart samples showing $\sim 2^{4.8\text{-}13.27}$ folds higher mTERT expressions than the non-treated control samples (Ctr).

The results showed that positive signals of 18s and GAPDH endogenous control were observed in all samples. Positive signals of mTERT were observed in all four OEGJ treated heart samples and GC1 cells. There were very low or almost no mTERT expressions in non-treated control heart samples. All four treated samples showed ~$2^{4.8-13.27}$ folds higher mTERT expressions than the non-treated control samples (FIG. 6). The indication of this result provided the possibility of controlled induction of TERT expression by OEGJ treatment.

To test whether the enhanced expression of cell survival genes and TERT would be translated to extended lifespan, we continued the experiment with above mentioned OEGJ-treated mice. It was found that the activities of the treated mice were more active and appeared significantly healthier. Life-threatening stress bearing ability of the treated mice was also significantly enhanced compared with that in the non-treated control animals. Accordingly, the average lifespan of the five remaining OEGJ-treated mice was averagely 763±108 days. By contrast the lifespan of the remaining 5 non-treated mice was averagely 610±158 days. In summary, the OEGJ treated mice enjoyed 17-25% longer lifespan than non-treated control (FIG. 6).

Example 5

OEGJ-Induced Improvement in Age-Related Disorders in Senescence-Accelerated Mouse The Senescence-Accelerated Mouse (SAM) strain was established in the Department of Senescence Biology, Kyoto University, Japan as a novel murine model of senescence acceleration and age-associated disorders. In the present study, short lived mice (SAMP10) were used. The SAMP10 mouse shows accelerated aging. The most characteristic age-related change in SAMP10 is brain atrophy, particularly in the frontal portion of the cerebrum, frontal, parietal, temporal and occipital cerebral cortices. The large neurons in these areas typically shrank and/or disappeared in aged SAMP10 (Shimada et al, 1992). All these characteristic pathological phenotypes are similar to age-associated disorders often observed in elder humans. SAMP10 mice have a median survival time of 333 days (Takeda et al, 1991).

When the SAMP10 mice were 4 months old, the mice in test group (n=16) were treated with OEGJ (400 mg/kg/day in H₂O suspension) through intragastric administration daily for 4 weeks. The mice in non-treated control group (n=16) were equivalently administered with water. One month after termination of the treatment, when the mice were 6 months old, Morris water maze (1.8M) was used to access the spatial learning and memory capacity in all mice of both groups. Animals were trained 5 times a day for 4 days. Typically, time spent in finding the platform was used to assess the strength of the learning ability and memory of the mouse for the platform location. The time spent prior to finding the hidden platform, also known as escape latency, was recorded. It was shown that OEGJ-treated SAMP10 mice exhibited a significantly shorter escape latency compared to the non-treated mice (P<0.001).

The cerebral blood flow (CBF) of the experimental mice was studied with a 12-MHz linear probe of the Toshiba ultrasound scanner after 4 weeks OEGJ treatment. To rule out the possibility of vessel dilation effect of OEGJ, after 4 weeks OEGJ treatment, the CBF was determined 2 weeks after the OEGJ treatment. The average of 3 repeated measurements was taken as the CBF. It was found that the CBF in OEGJ-treated mice was on average 15% higher than that in non-treated control mice. Interestingly, the net weight of the brain in OEGJ mice was on average about 15% heavier than that of non-treated mice by the time when the mice were sacrificed after water maze test. Furthermore, the blood pressure in non-treated mice was about 135 mmHg, which was about 13% higher than that in normal mice. In comparison, the blood pressure of OEGJ treated SAMP10 mice was about 10% lower than that of non-treated counterparts. These results suggest that OEGJ treatment induced new collateral vessel formation in the brain of the mice that reduced the peripheral resistance of arterioles or microvessels so that significant more blood flow to the brain could be achieved.

In order to confirm the physical basis for the increased CBF in OEGJ-treated animals, brains from the experimental mice sacrificed after CBF measurement were removed, fixed in formalin and embedded in paraffin. Thin sections (5 μm) were cut from each slide and stained with H&E staining. The vascular densities were determined on the histology sections by counting the numbers of vessels within the cortex of frontal lobe and around hippocampus regions. Six random and non-overlapping high power fields (HPFs) (40×) within the frontal lobe or hippocampus were used for counting all the vessels in each section. The number of vessels in each HPF was averaged and expressed as the number of vessels per HPF. Vascular counts were performed by two investigators in a blind fashion.

Figure 7:
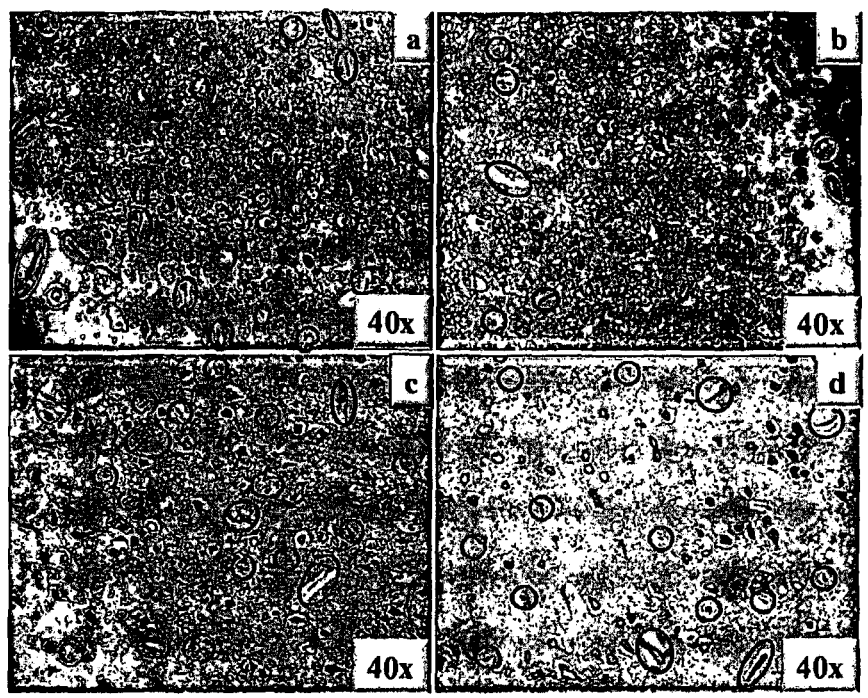
FIG. 7, The OEGJ treatment induced neoangiogenesis in brains of SAMP10 mice. a, Significantly more (15-25%) blood vessels (circles) were observed around hippocampus region of the OEGJ treated mice. b, By contrast, fewer vessels were found around the hippocampus region of non-treated control mice (circles). c, More (15-25%) vessels were observed in cortex region of frontal lobe in OEGJ treated mice (circles). d, Fewer vessels were found in the same region in non-treated control animals (circles).

The result of vessel counting showed that the numbers of vessels are about 68.6±16.3/HPF in the regions of cortex in frontal lobe and 46.8±13.2/HPF around the regions of hippocampus in non-treated control mice (FIG. 7). By contrast, the numbers of vessels are about 83.8±12.9/HPF in cortex region of frontal lobe and 61.7±11.2/HPF around hippocampus region in OEGJ treated mice (FIG. 7).

Figure 8:
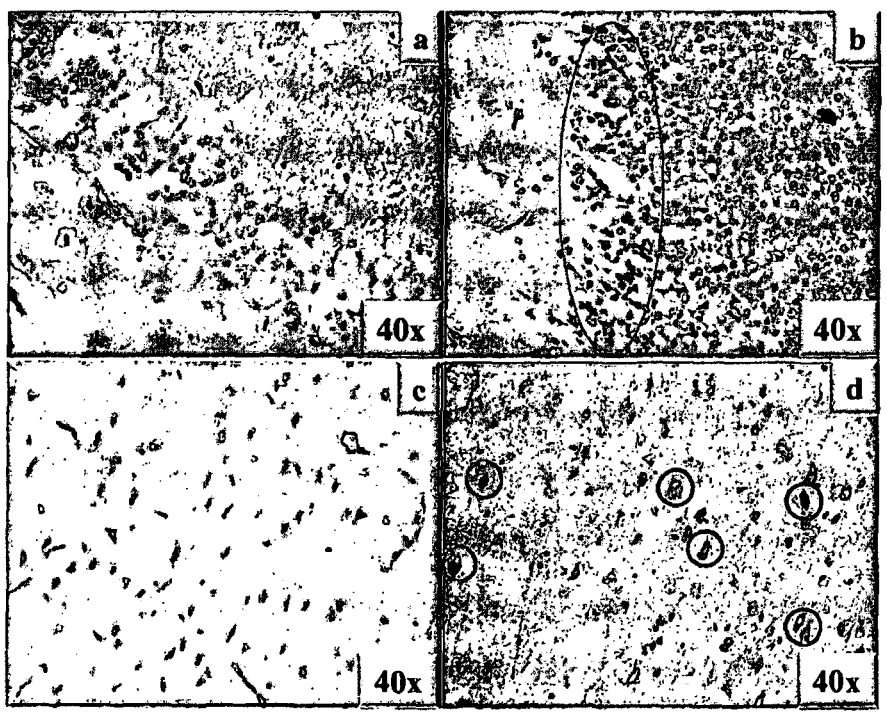
FIG. 8, The OEGJ treatment induced neuronal regeneration in SAMP10 mice. a, Almost no positive Ki67 signals were observed in the hippocampus region of the non-treated control mice. b, Some dark brown Ki67 positive signals (circled) with the shape of nuclei of granule cells were found in the inner edge of the DG region of hippocampus in OEGJ treated animals indicating neuronal regeneration. c, Almost no Ki67 positive signals were found in cortex region of frontal lobe of the non-treated control mice. d, Some Ki67 positive signals with the shape of neurons (red circles) were identified in cortex region of frontal lobe in OEGJ treated mice.

To investigate whether OEGJ treatment induced improvement of microcirculation in brain would bring about neural regeneration to replace the damaged or died neurons, thin sections (5 μm) were cut from each slide of brain obtained from experimental mice and immunohistochemically stained with specific antibodies against Ki67. On microscope examination of the sections, it was found that OEGJ treatment not only enhanced the growth of new blood vessels in the regions of cortex and hippocampus, but also induced neuronal regeneration in these regions (FIG. 8). By contrast, no significant growth of new collateral vessels in the brain was identified and neither the regeneration of new neuron cells in the non-treated control brains (FIG. 8). The newly regenerated neuron-like cells were positively stained with antibodies specific to Ki67 (FIG. 8) indicating that they are newly regenerated neuronal cells.

In sum, these observations imply that OEGJ not only stimulated the substantial growth of new collateral vessels in the brain of SAM mice resulting in improved CBF, but also induced neuronal regeneration in the cortex of frontal lobe and hippocampus regions that are responsible for learning and cognitive abilities, which may be the physical basis for the substantially improved performance in water maze exploration tests. In summary, it appeared that OEGJ can reduce the progress of aging process or even can reverse aging by stimulating reconstitution of the microcirculation, in which cells live and function, and replacing the damaged or died important cells, such as neurons or cardiac myocytes with newly regenerated neurons or cardiac myocytes. Therefore, the compositions of the present invention may be used for enhancing longevity and quality of life.

Example 6

Diabetes

Based on the above-mentioned rationale, the possibility of using OEGJ for the treatment of diabetes was tested in diabetics on the basis of mercy treatment. A 59-year-old male was first diagnosed with diabetes before undergoing hemorrhoid surgery a year before treatment. His blood glucose level at that time was 24.0 mmol/L. He was put on insulin treatment for a week and started to take diabetes medicine (Diamicron 80 mg, 2 tablets every morning under fasting condition). His average blood glucose level during the six-month period on the medication was 9.97 mmol/L. He started to take OEGJ orally (1.8 g/daily) in combination with Daimicron and his average blood glucose level during the two-month period of OEGJ treatment was lowered to 7.90 mmol/L. His average blood glucose level was kept at a similar level (8.06 mmol/L) even after he discontinued with OEGJ treatment for two months.

Example 7

Inflammatory Diseases, Wound Healing and Bedsore

Based on the above-mentioned therapeutic effects, OEGJ should be useful in treating chronic inflammatory diseases, wounds and bedsores. We therefore tested the possibility of using OEGJ for the treatment of chronic inflammatory diseases, wounds and bedsores on the basis of mercy treatment.

A female patient from Shanghai had multiple brain attacks (strokes) about two years ago. After she had another brain attack about 8 months ago, she completely lost her language and all physical abilities. She lost any proactive reaction to any events and appeared as a complete vegetative patient with muscle stiffness. A few months later, she developed a deep bedsore (16-18 cm diameter and 10-12 cm deep) on the buttocks at the time of examination. What made the situation even worse was that the patient was also infected with multipledrug-resistant *Staphylococcus aureus*. People were worried she would lose her life from this severe bedsore and infection. After surgical debridement of the dead and decayed tissues, she was administered with OEGJ (oral administration, 2 grams/day). One week after OEGJ medication, her bedsore began to heal very quickly. The open wound became smaller and progressively shallower. Two months treatment with OEGJ had completely healed her deep decubitus. When the patient stopped taking the drug, the speed of healing of her bedsore was slowed down. After the patient resumed the OEGJ treatment, the speed of healing of the bedsore was accelerated.

Example 8

Ocular Disorders

Based on the above-mentioned rationale, the possibility that OEGJ may be useful in treating age-related and degenerative ocular disorders was tested in patients on the basis of mercy treatment.

An 80 years old female, started to show symptoms of cataract four years ago. Her vision is getting worse that she could not see pictures on TV clearly even with glasses. She received OEGJ (2 g/daily) by oral administration for one month. Three months later, she claimed that she could watch TV with no difficulties even without glasses. She could also read magazines and books well.

A 78-year-old male was diagnosed with severe cataract over a year with blurred vision and became blind eventually. After cataract surgery, his vision was recovered somewhat. However, he completely lost his vision again two weeks later. Three months after cataract surgery, he was treated with OEGJ (1.5 g/daily) orally for two months. After OEGJ treatment, he could clearly identify individual persons and be able find his way while walking. He was even able to identify small objects (3 cm long and 0.3 cm in diameter) in the vegetable field.

A 48-year-old female has been wearing reading glasses due to presbyopia for over eight years. Eight months ago, she had to wear more powerful reading glasses to be able to see clearly the contents on the computer. After one month oral administration of OEGJ (0.5 g/daily), she was able to read articles on the computer even without glasses.

A 48-year-old male started to complain about vision problems due to presbyopia about four years ago. Without reading glasses, he could not see details on his identification card clearly. After oral administration of OEGJ (2 g/daily) for two months, he could read his identification card with no difficulties even without his reading glasses.

Based on the above-mentioned multiple therapeutic effects of OEGJ and the promising effects of OEGJ in treating people with ocular disorders, we propose that OEGJ may exert its effects by significantly promoting physical reconstitution of insufficient blood supply due to aging that will substantially improve the living micro-environment of tissues and cells in the eye. In case of cataract, by increasing blood flow in the eye, OEGJ may help to prevent and/or slow down the protein clustering on the lens and may be also helpful in dissolving the preexisting protein clusters on the lens. In case of presbyopia, OEGJ-induced improvement of micro-environment may be beneficial for keeping the elasticity of the lens and enhancing the strength of ciliary muscles that are responsible for bending and straightening the lens. In line with this notion, OEGJ may also be useful for treating other ocular disorders such as diabetic retinopathy, retinitis pigmentosa and ocular ischemic syndrome.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

Armanios M Y, Chen J J, Cogan J D, Alder J K, Ingersoll R G, Markin C, Lawson W E, Xie M, Vulto I, Phillips J A 3rd, Lansdorp P M, Greider C W, Loyd J E. Telomerase mutations in families with idiopathic pulmonary fibrosis. *N Engl J Med* 356: 1317-1326, 2007.

Artandi S E, Alson S, Tietze M K, Sharpless N E, Ye S, Greenberg R A, Castrillon D H, Horner J W, Weiler S R, Carrasco R D, DePinho R A. Constitutive telomerase expression promotes mammary carcinomas in aging mice. *Proc Natl Acad Sci USA* 99: 8191-8196, 2002.

Artandi S E, Chang S, Lee S L, Alson S, Gottlieb G J, Chin L, DePinho R A. Telomere dysfunction promotes non-reciprocal translocations and epithelial cancers in mice. *Nature* 406: 641-645, 2000.

Artandi S E, DePinho R A. A critical role for telomeres in suppressing and facilitating carcinogenesis. *Curr Opin Genet Dev* 10: 39-46, 2000.

Autexier C, Lue N F. The structure and function of telomerase reverse transcriptase. *Annu Rev Biochem* 75: 493-517, 2006.

Autexier C, Lue N F. The structure and function of telomerase reverse transcriptase. *Annu Rev Biochem* 75: 493-517, 2006.

Baerlocher G M, Lansdorp P M. Telomere length measurements in leukocyte subsets by automated multicolor flow-FISH. *Cytometry A* 55: 1-6, 2003.

Baerlocher G M, Rice K, Vulto I, Lansdorp P M. Longitudinal data on telomere length in leukocytes from newborn baboons support a marked drop in stem cell turnover around 1 year of age. *Aging Cell* 6: 121-123, 2007.

Baerlocher G M, Vulto I, de Jong G, Lansdorp P M. Flow cytometry and FISH to measure the average length of telomeres (flow FISH). *Nat Protocol* 1: 2365-2376, 2006.

Baird D M, Davis T, Rowson J, Jones C J, Kipling D. Normal telomere erosion rates at the single cell level in Werner syndrome fibroblast cells. *Hum Mol Genet* 13: 1515-1524, 2004.

Baird D M, Rowson J, Wynford-Thomas D, Kipling D. Extensive allelic variation and ultrashort telomeres in senescent human cells. *Nat Genet* 33: 203-207, 2003.

Collins K. The biogenesis and regulation of telomerase holoenzymes. *Nat Rev Mol Cell Biol* 7: 484-494, 2006.

Cooke H J, Smith B A. Variability at the telomeres of the human X/Y pseudo autosomal region. *Cold Spring Harb Symp Quant Biol* 51: 213-219, 1986.

Counter C M, Avilion A A, LeFeuvre C E, Stewart N G, Greider C W, Harley C B, Bacchetti S. Telomere shortening associated with chromosome instability is arrested in immortal cells which express telomerase activity. *EMBO J* 11: 1921-1929, 1992.

Harley C B, Futcher A B, Greider C W. Telomeres shorten during ageing of human fibroblasts. *Nature* 345: 458-460, 1990.

Hastie N D, Dempster M, Dunlop M G, Thompson A M, Green D K, Allshire R C. Telomere reduction in human colorectal carcinoma and with ageing. *Nature* 346: 866-868, 1990.

Hayflick L. Living forever and dying in the attempt. *Exp Gerontol* 38: 1231-1241, 2003.

Hornsby P J. Short telomeres: cause or consequence of aging? *Aging Cell* 5: 577-578, 2006.

J. Apfeld and C. Kenyon (1998) Cell non-autonomy of C. elegans daf-2 function in the regulation of diapause and lifespan, *Cell*, v. 95, n.2, pp. 199-210.

J. B. Dorman, B. Albinder, T. Shroyer & C. Kenyon (1995) The age-1 and daf-2 genes function in a common pathway to control the lifespan of *Caenorhabditis elegans*, *Genetics*, volume 141, number 4, pages 1399-1406.

J. McElwee, K. Bubb, J. H. Thomas (2003) Transcriptional outputs of the *Caenorhabditis elegans* forkhead protein DAF-16. *Aging Cell* 2: 111-121.

Lei Cheng, Hao Chen, Xinsheng Yao, Guoqing Qi, Hongwei Liu, Kwongman Lee, Kaho Lee, Jieting Zhang, Shihui Chen, & Ming Li (2009) A Plant-derived remedy for repair of infarcted heart. *Plos One*, V4(2)|e4461.

M. S. Gami and C. A. Wolkow (2006) Studies of *Caenorhabditis elegans* DAF-2/insulin signaling reveal targets for pharmacological manipulation of lifespan, *Aging Cell* 5 (1): 31.

Shimada, A. Ohta, I. Akiguchi, T. Takeda (1992) Inbred SAM-P/10 as a mouse model of spontaneous, inherited brain atrophy. *J. Neuropathol. Exp. Neurol.* 51, 440-450.

S. T. Henderson and T. E. Johnson (2001) daf-16 integrates developmental and environmental inputs to mediate aging in the nematode *Caenorhabditis elegans*. Current Biology 11: 1975-1980.

S. W. Oh, A. Mukhopadhyay, B. L. Dixit, T. Raha, M. R. Green, et al. (2006) Identification of direct DAF-16 targets controlling longevity, metabolism and diapause by chromatin immunoprecipitation. Nature Genetics 38: 251-257.

T. Takeda, M. Hosokawa, K. Higuchi (1991) Senescence-accelerated mouse (SAM): A novel murine model of accelerated senescence. *J. Amer. Geriatr. Soc.* 39, 911-919.

Von Zglinicki T. Role of oxidative stress in telomere length regulation and replicative senescence. *Ann NY Acad Sci* 908: 99-110, 2000.

What is claimed is:

1. A method for increasing longevity in a non-diseased animal subject, the method comprising administering to the subject an effective amount of an organic extract of *Geum japonicum* (OEGJ), wherein the effective amount of the extract is at least 200 mg/kg/day, and wherein the organic extract is a methanol extract or an ethanol extract.

2. The method of claim 1, wherein the extract stimulates expression of telomerase and one or more cell survival factors selected from the group consisting of: Akt1, Bcl2, EGF, VEGF and NFκB.

3. The method of claim 1, wherein the subject is a human.

4. The method of claim 1, wherein the extract is administered orally.

5. The method of claim 1, wherein the extract is administered by subcutaneous injection, intramuscular injection, or intravenous infusion.

6. The method of claim 1, wherein the extract is administered in a formulation, wherein the formulation comprises a pharmaceutically acceptable carrier.

\* \* \* \* \*